(12) United States Patent
Monjazeb

(10) Patent No.: US 10,456,127 B2
(45) Date of Patent: Oct. 29, 2019

(54) RETRACTABLE SUTURE NEEDLE ASSEMBLY

(71) Applicant: Seena Monjazeb, Friendswood, TX (US)

(72) Inventor: Seena Monjazeb, Friendswood, TX (US)

( * ) Notice: Subject to any disclaimer, the term of this patent is extended or adjusted under 35 U.S.C. 154(b) by 157 days.

(21) Appl. No.: 15/646,064

(22) Filed: Jul. 10, 2017

(65) Prior Publication Data

US 2018/0008259 A1    Jan. 11, 2018

Related U.S. Application Data

(60) Provisional application No. 62/360,181, filed on Jul. 8, 2016.

(51) Int. Cl.
*A61B 17/06* (2006.01)
*A61B 17/04* (2006.01)
*A61B 17/062* (2006.01)

(52) U.S. Cl.
CPC ...... *A61B 17/0493* (2013.01); *A61B 17/0625* (2013.01); *A61B 17/06066* (2013.01); *A61B 2017/06052* (2013.01)

(58) Field of Classification Search
CPC .......... A61B 17/06066; A61B 17/0625; A61B 17/0493
See application file for complete search history.

(56) References Cited

U.S. PATENT DOCUMENTS 3,249,104 A * 5/1966 Hohnstein ........ A61B 17/06004
                                                   223/102
5,236,443 A * 8/1993 Sontag ............... A61B 17/0482
                                                   606/223

* cited by examiner

*Primary Examiner* — Kathleen S Holwerda
*Assistant Examiner* — Christina C Lauer
(74) *Attorney, Agent, or Firm* — Law Office of Jeff Williams PLLC; J. Oliver Williams

(57) ABSTRACT

An assembly and method for the protection of medical personnel from accidental suture needle sticks is described. The assembly includes a case containing a needle which can be retracted when not in use. The needle is extended and retracted through the engagement of a needle driver which compresses a compressible member. The compressible member exerts a force on the needle which in turn extends the needle's point beyond the casing so that the user can suture tissue. Disengaging the needle driver retracts the needle point which protects the user from accidentally receiving a needle prick from a contaminated needle between punctures.

13 Claims, 6 Drawing Sheets

RETRACTABLE SUTURE NEEDLE ASSEMBLY

CLAIM OF PRIORITY

This application claims the benefit of U.S. Provisional Application No. 62/360,181, filed 8 Jul. 2016. The information contained therein is hereby incorporated by reference.

BACKGROUND

1. Field of the Invention

The present application relates generally to a medical device, and in particular to a retractable suture needle assembly that prevents the incidence of accidental needle stick by the user.

2. Description of Related Art

Injuries among healthcare personnel, due to sharps, is an area of concern because sharps pose a risk of transmission of blood-borne disease such as hepatitis B, hepatitis C and human immunodeficiency virus (HIV). A sharp is defined as an object with a fine point to poke a hole, such as a needle point, or a thin edge capable of cutting, such as a scalpel. The Center for Disease Control (CDC) estimates 385,000 sharps injuries occur annually among hospital based personnel. Sharps injuries represent a large expense both to the individual health care giver and the healthcare industry. Some of the direct costs of sharps injuries include laboratory testing and follow up treatment of the user, which is estimated to range between $71 to $5000 per person. If a disease is contracted as the result of a sharps injury, treatment of the disease as well as resulting lawsuits drive the cost even higher.

Suture needles are involved in about 20% of sharps injuries. Current suturing equipment leaves the needle exposed while medical personnel are tying knots or disposing of the suture needle. Methods to prevent suture needle sticks include the proper disposal of the needles after use and the use of blunt-tip suture needles when suturing fascia and muscle.

Although great strides have been made in preventing suture sticks, considerable shortcomings remain. A new system is required that ideally prevents suture needle sticks.

DESCRIPTION OF THE DRAWINGS

The novel features believed characteristic of the application are set forth in the description. However, the application itself, as well as a preferred mode of use, and further objectives and advantages thereof, will best be understood by reference to the following detailed description when read in conjunction with the accompanying drawings, wherein.

Figure 1:
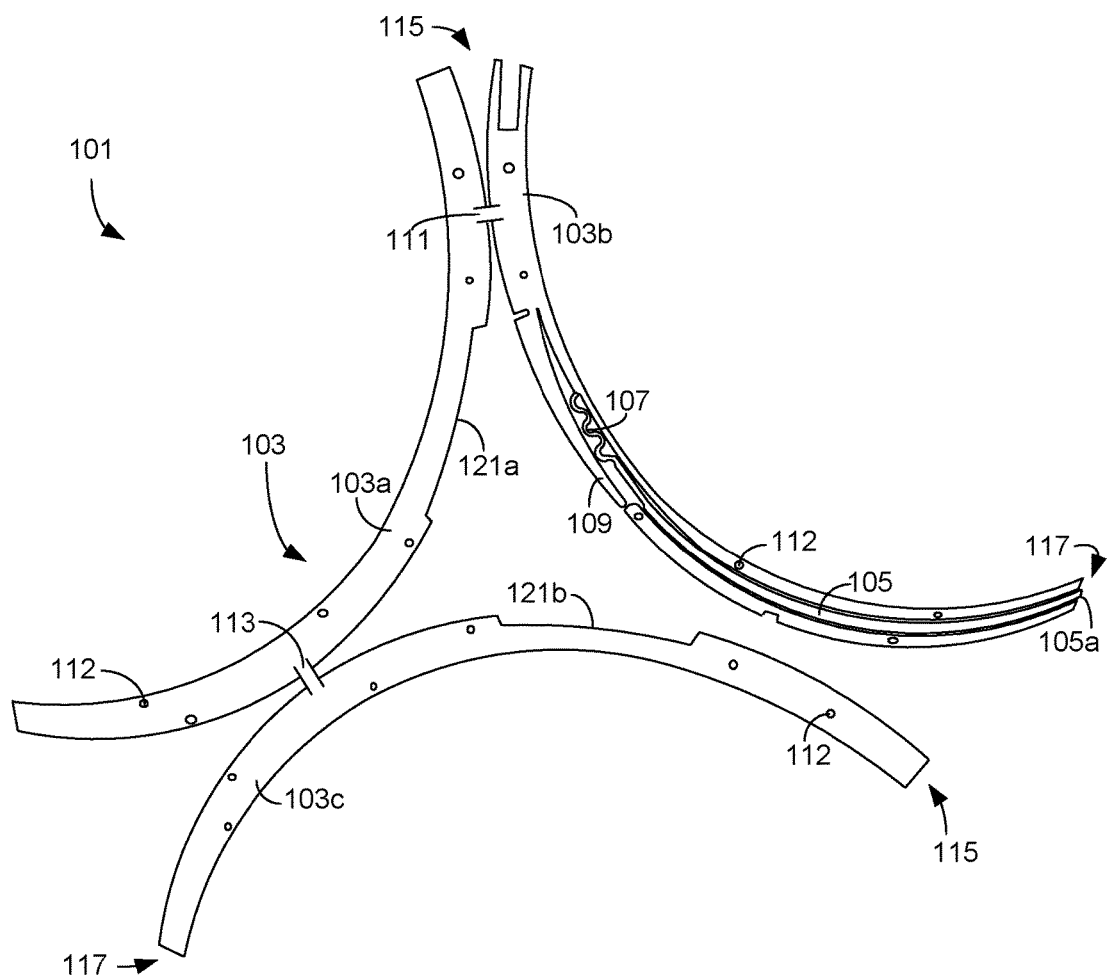
FIG. 1 is top view of a retractable suture needle assembly prior to assembly.

While the assembly and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms to describe a spatial relationship between various components or to describe the spatial orientation of aspects of such components should be understood to describe a relative relationship between the components or a spatial orientation of aspects of such components, respectively, as the device described herein may be oriented in any desired direction.

The assembly and method in accordance with the present application overcomes one or more of the above-discussed problems commonly associated with conventional suture needles. Specifically, the retractable suture needle assembly is configured to assist in preventing an accidental needle stick when the suture needle is not in use. The suture needle is configured to selectively extend and retract into a casing when in use. These and other unique features of the device are discussed below and illustrated in the accompanying drawings.

The assembly and method will be understood, both as to its structure and operation, from the accompanying drawings, taken in conjunction with the accompanying description. Several embodiments of the assembly may be presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless otherwise described.

The assembly and method of the present application is illustrated in the associated drawings. The assembly includes a three-part casing configured to surround a suturing needle and protect the user from an accidental needle stick. The assembly includes a mechanism to extend the needle out of the casing and allow the needle to retreat into the casing after use. The mechanism includes a needle driver in communication with an inner casing member and configured to flex under the application of pressure to selectively operate the suturing needle. The needle driver compresses a compressible member which exerts a force on the needle. The needle extends away from the casing when the compressible member exerts a force on it. In a resting state, the compressible member retracts the suturing needle. Additional features and functions of the device are illustrated and discussed below.

Referring now to the drawings wherein like reference characters identify corresponding or similar elements in form and function throughout the several views. FIG. 1 illustrates a top view of a retractable suture needle assembly 101 prior to assembly. The assembly 101 is comprised of a casing 103, a needle 105, a compressible member 107, and a needle driver 109. Assembly 101 is used to protect users from blood borne pathogens that may be passed if the user's skin is broken by a surgical instrument. Assembly 101 is configured to the approximate size of a normal surgical needle.

The casing 103 is comprised of three sub-casings: outer casing 103a, inner casing 103b, and outer casing 103c. In the current embodiment, casing 103b is coupled to casing 103a by a back hinge 111 and casing 103a is coupled to casing 103c by a front hinge 113. Back hinge 111 is located adjacent to a suture end 115 of casing 103 (see FIG. 3) and front hinge 113 is adjacent to a point end 117 of casing 103 (see FIG. 3). Hinges 115 and 117 are used to pivot casings 103a, 103b, and 103c into place. It is understood that casings 103a, 103b, and 103c are connected by at least one hinge and the hinge may be placed in any location which facilitates the assembly of casing 103.

Casing 103 is assembled by the pivoting of casings 103a, 103b, 103c in a particular order. Casing 103b is configured to pivot about hinge 111 and rest against casing 103a. Furthermore, casing 103c is configured to pivot about hinge 113 and rest against casing 103b. When assembled in such manner, casing 103 is fully formed. Casings 103a and 103c are configured to cover opposing sides of casing 103b. Casing 103 may be secured in an assembled configuration by any number methods. Examples of the types of couplings are interference fit, snaps, clips, fasteners, or tying by a line. If a line is used, the line may pass through interrelated holes 112 in each of the casing members. Casings 103a, 103b, and 103c are selectively disassembled such that casing 103 can be more easily be cleaned or repaired as needed.

The compressible member 107 is attached at one end to a base of needle 105 and at an opposing end it is coupled to casing 103b. Therefore, compressible member 107 is in communication with both casing 103b and needle 105. Needle driver 109 is also coupled at one end to casing 103b above compressible member 107. A user engages driver 109 to compress the compressible member 107 to selectively position needle 105 between an extended position and a retracted position. Until the user engages driver 109, point 105a of needle 105 remains retracted within casing 103 and the user is protected from an accidental needle prick. Needle 105 is used to pierce tissue and create a hole for the suture 119 (see FIG. 2) to transition through.

Figure 2:
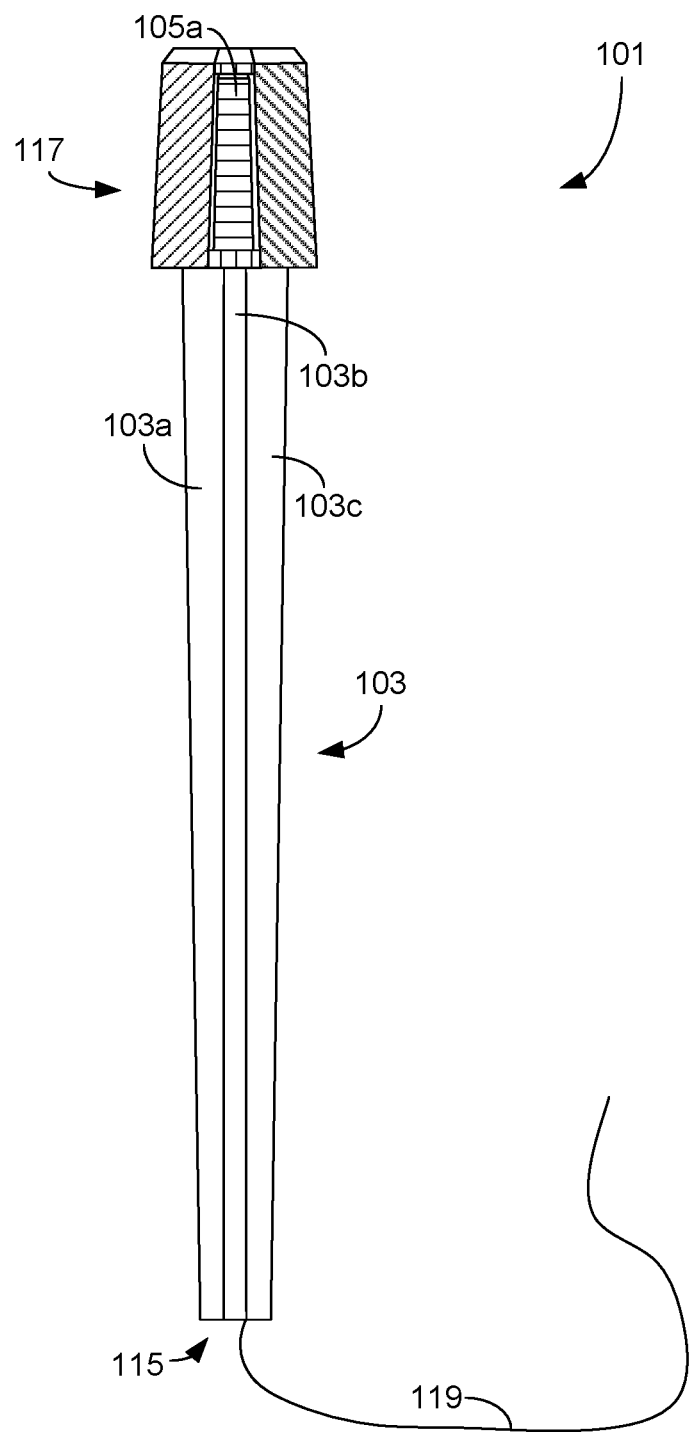
FIG. 2 is a front view of the retractable suture needle assembly of FIG. 1 as assembled.
Figure 3:
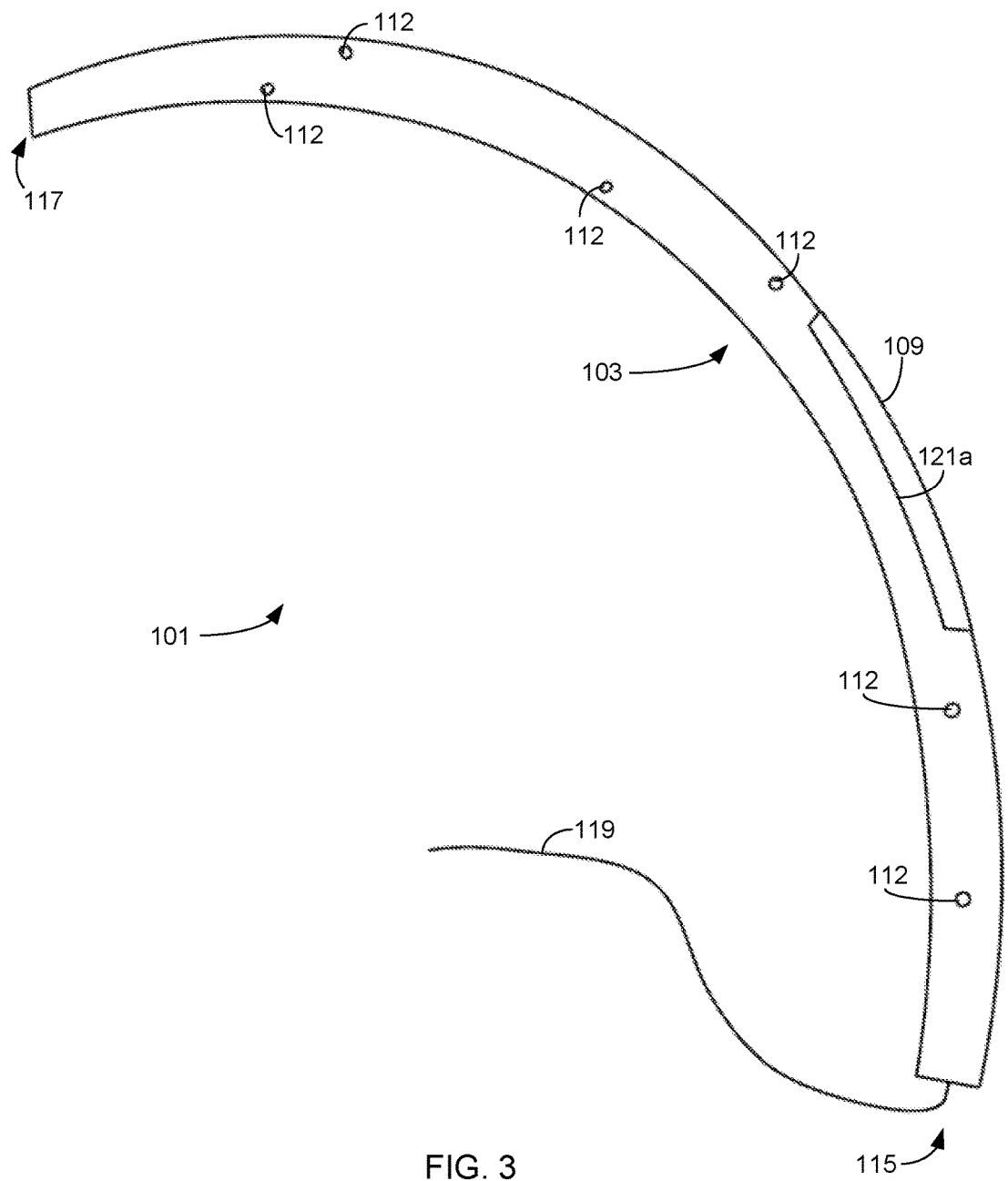
FIG. 3 is a side view of the retractable suture needle assembly of FIG. 1 as assembled.

Referring now also to FIGS. 2-3 in the drawings, a front and side view respectively of assembly 101 are illustrated. Casing 103 is depicted in FIGS. 2-3 with a suture 119. Suture 119 is comprised of any material commonly used in surgical suturing. In the current embodiment, casing 103 is assembled by pivoting casing 103b about hinge 111, and then pivoting casing 103c about hinge 113, such that casing 103b is situated between casings 103a and 103c. While casing 103 is depicted to be formed from three pieces, casing 103a, 103b, and 103c, it is understood that casing 103 may be formed by combining any number of sub-casings together. Additionally, hinges are placed at locations needed to facilitate the formation of casing 103.

As seen in particular with FIG. 3 in the drawings, casings 103a and 103c are notched in the same relative location creating a cut-out 121a and 121b. Cut-outs 121a and 121b are equally located along the perimeter of casing 103 on opposing sides of driver 109, such that driver 109 is fully exposed. Cut-outs 121a and 121b facilitate the user's engagement of driver 109. As also seen in FIG. 1, casings 103a, 103b, and 103c have matching holes 112. Holes 112 are aligned with each other when casings 103 is formed so as to extend all the way through casing 103.

As seen in FIG. 2, needle 105 has a rectangularly shaped point 105a. It is understood that the shape of needle 105, and its point 105a, may be configured in additional shapes, including round, oval, and triangular. The shape of needle 105, and its point 105a, are configured to facilitate the purpose of creating a hole for suture 119 to transition through.

Suture 119 attaches to casing 103 at suture end 115. Suture end 115 is located opposite from the point end 117 of casing 103. Suture end 115 provides a place for suture 119 to communicate to casing 103. It is understood that suture 119 will communicate to casing 103 in a fashion commonly used in the surgical community.

Figure 4:
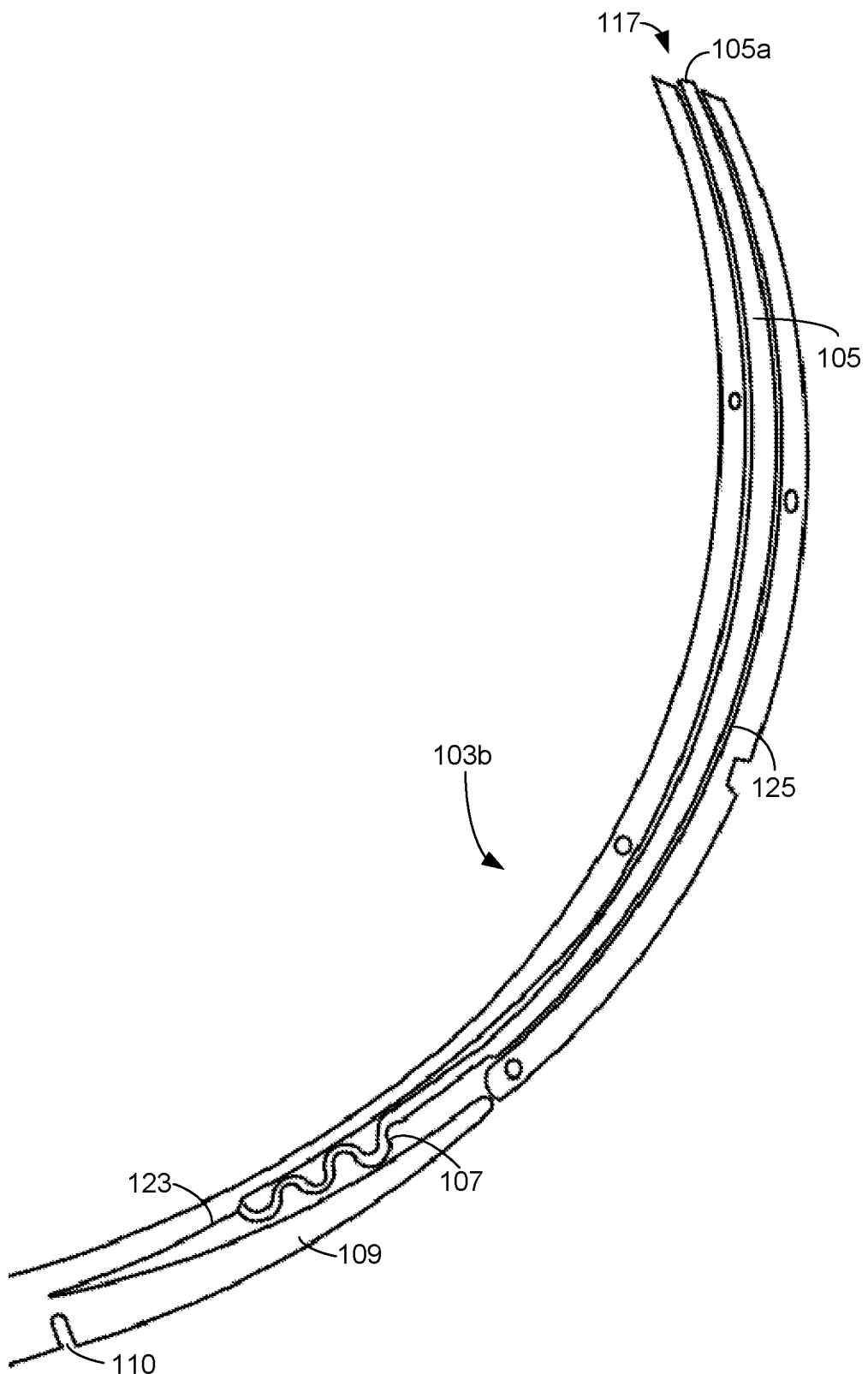
FIG. 4 enlarged side view of an inner casing of the retractable suture needle assembly of FIG. 1.
Figure 5:
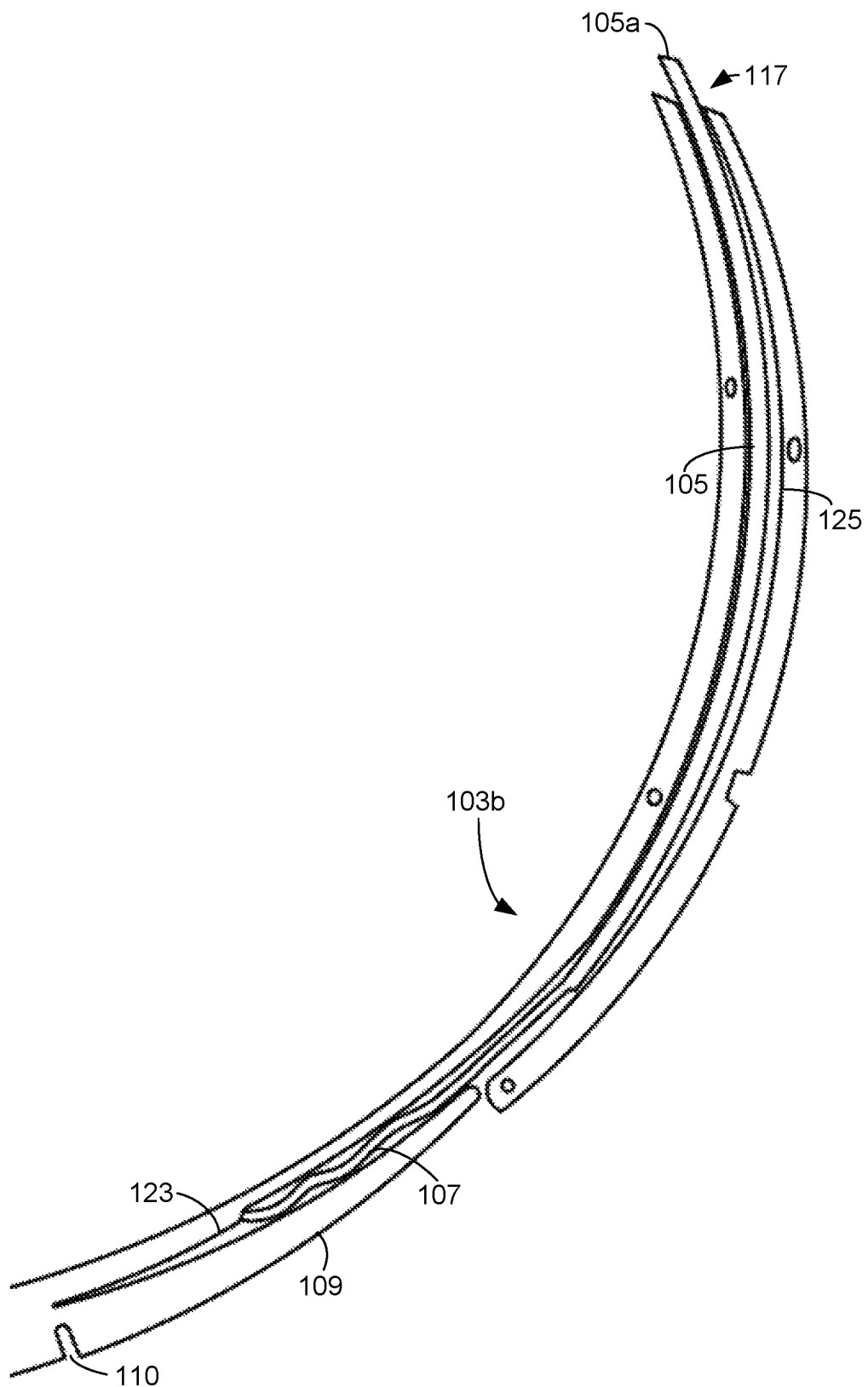
FIG. 5 an alternative side view of the inner casing of FIG. 4 with a needle extended.

Referring now also to FIGS. 4-5 in the drawings, enlarged views of casing 103b with needle 105 retracted and extended, respectively, are illustrated. In this embodiment, driver 109 is depicted as a single tab flexibly coupled to casing 103b. The coupling is located at one end (base end) of the driver and allows the user to engage the driver 109 such that driver 109 selectively compresses the compressible member 107 when engaged upon by a user. A notch 110 is located adjacent its base end to aid in facilitating is flexure. It is understood that driver 109 may be attached at different locations on casing 103b or casings 103a or 103c. Additionally, driver 109 may be flush with the outer contour of casing 103 or it may be raised above the outer contour of casing 103. Driver's 109 configuration will facilitate the user's ability to engage or disengage with driver.

In this embodiment, compressible member 107 is attached at one end to a base of needle 105 and at an opposing end it is coupled to casing 103b. The compressible member 107 is configured to locate needle 105 between an extended position and a retracted position. As depicted, member 107 is a wave spring with one or more waves. In operation, as driver 109 is flexed, member 107 is compressed between driver 109 and a bottom inner surface 123 of casing 103b. Compression of the waves results in the lengthening of the spring which in turn translates needle 105 through a passaged formed by casings 103a, 103c, bottom inner surface 123 and an upper inner surface 125 of casing 103b. When driver 109 is unflexed, the waves of member 107 return to their relaxed and shortened length which in turn locates needle 105 back in a retracted position. FIG. 4 shows the retracted position wherein point end 105a is located within casing 103. FIG. 5 shows the extended position wherein point end 105a is located outside of casing 103.

Of note, point 105a is not depicted as being flush with the point end 117 when extended. It is understood that point end 117 can be configured such that point 105a, when extended, and point end 117 are flush and create a smooth transition. Casing 103 at point end 117 can be selectively tapered and contoured to maintain a smooth transition between needle point 105a and casing 103 when needle 105 is extended.

Figure 6:
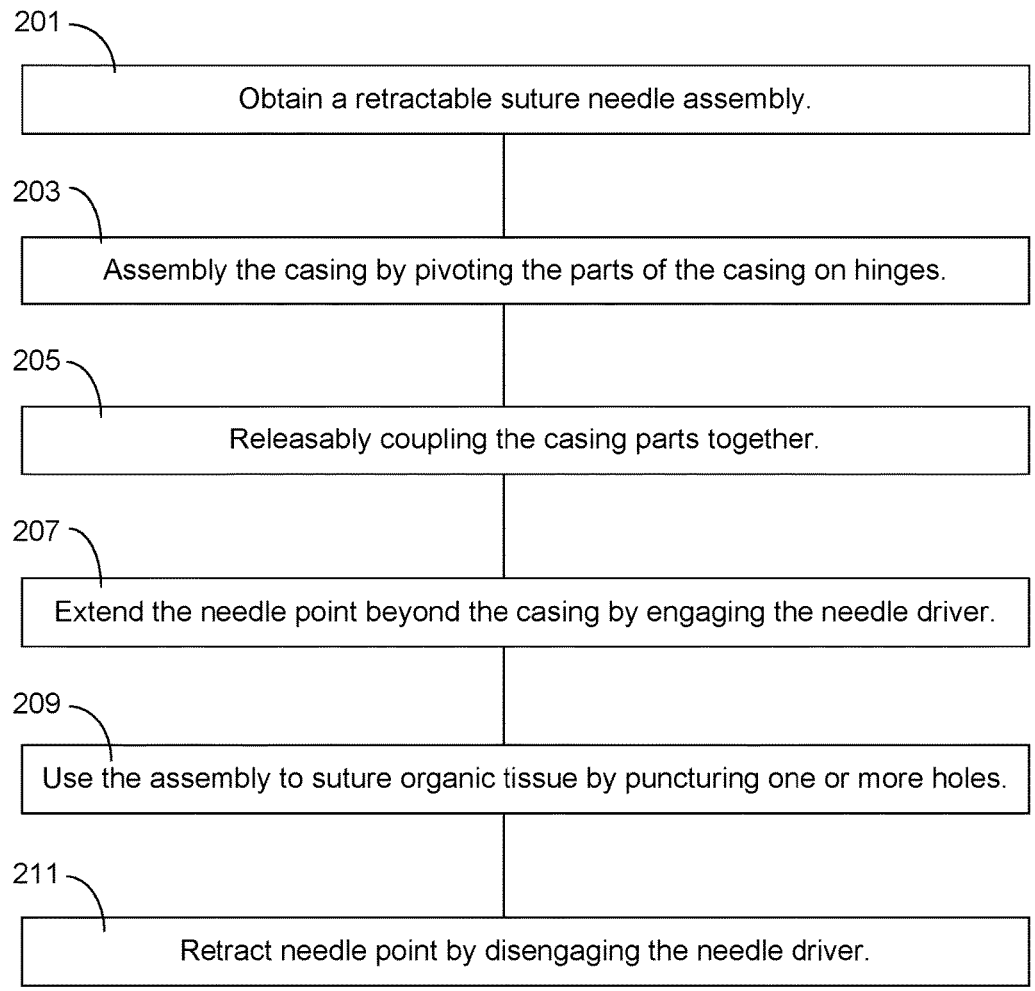
FIG. 6 is a flow chart for the use of the retractable suture needle assembly of FIG. 1.

Referring now also to FIG. 6, demonstrating the method for operation of the retractable suture needle assembly. The user obtains a retractable suture needle assembly, step 201. If the assembly is not assembled, the user assembles the retractable suture needle assembly by pivoting parts of the casing on hinges, step 203. The user releasably couple the casing parts together, step 205. It is understood that the casing parts can be secured together through any method commonly used, such as interference fit, snaps, clips, fasteners, or tying by a line. When desired, the user extends the needle point beyond the casing by engaging the needle driver, step 207. The user engages the needle driver by applying pressure to the needle driver either by squeezing the needle driver and casing between the user's fingers or a type of surgical tool. It is understood that the pressure applied to the needle driver compresses the compressible member between the needle driver and the bottom interior surface of the casing. The compression results in the compressible member exerting a force on the needle which pushes the needle point away from the casing. Once the needle point is extended, the user can use the retractable suture needle assembly, like a normal surgical suture needle, to suture together organic tissue, step 209. Once the user is finished with suturing, the user retracts the needle point by disengaging the pressure from the needle driver, step 211.

The current application has many advantages over the prior art including at least the following: (1) The needle point can be retracted when needed; (2) a reduction in the risk of an accidental needle puncture which can result in the transmission of blood-born pathogens; and (3) it is easy to use due to its similar size and shape to a standard suturing needle.

The particular embodiments disclosed above are illustrative only, as the application may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

What is claimed is:

1. A retractable suture needle assembly, comprising:
    a casing including a plurality of outer casings and an inner casing hingedly coupled together, the plurality of outer casings configured to selectively surround a portion of the inner casing;
    a needle located within the inner casing;
    a compressible member within the inner casing and coupled to a base of the needle, the compressible member also coupled to the inner casing at an end opposite the base of the needle, the compressible member configured to position the needle in at least one of an extended position and a retracted position; and
    a needle driver pivotally coupled to the inner casing and surrounded by the outer casings, the needle driver configured to selectively flex and apply a pressure to the compressible member so as to adjust the location of the needle relative to the casing.

2. The assembly in claim 1, wherein the casing remains comparable in size to a standard suturing needle.

3. The assembly in claim 1, wherein the casing is assembled by pivoting the inner casing and the plurality of outer casings about a plurality of hinges.

4. The assembly in claim 1, wherein the casing is releasably coupled together between an assembled configuration and a disassembled configuration.

5. The assembly in claim 4, wherein casing is assembled together by interference fit.

6. The assembly in claim 4, wherein casing is assembled together by tying lines passed through holes.

7. The assembly in claim 1, wherein the needle extends out of a point end of the casing.

8. The assembly in claim 1, wherein a suture end of the casing is in communication with a suturing material.

9. The assembly in claim 1, wherein the needle driver is configured to pivot about a base end.

10. The assembly in claim 9, wherein the needle driver includes a notch at the base end to facilitate flexure.

11. The assembly in claim 1, wherein the compressible member comprises a spring.

12. The assembly in claim 11, wherein the spring is a wave spring.

13. The assembly in claim 1, wherein the compressible member is configured to translate the needle within a passage defined in the casing.

* * * * *